(12) United States Patent
Zhang et al.

(10) Patent No.: US 7,780,620 B2
(45) Date of Patent: Aug. 24, 2010

(54) SYSTEM AND METHOD FOR DETERMINING THE HEMATOCRIT AND/OR BLOOD VOLUME

(75) Inventors: Wei Zhang, Niederwerrn (DE); Helge Brauer, Heppenheim (DE); Reiner Spickermann, Burghausen (DE); Carsten Müller, Euerbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 655 days.

(21) Appl. No.: 11/717,812

(22) Filed: Mar. 13, 2007

(65) Prior Publication Data

US 2008/0015486 A1  Jan. 17, 2008

Related U.S. Application Data

(63) Continuation of application No. 10/507,033, filed as application No. PCT/EP03/00126 on Jan. 9, 2003, now abandoned.

(30) Foreign Application Priority Data

Mar. 7, 2002  (DE) .................................. 102 10 009

(51) Int. Cl.
*A31M 37/00* (2006.01)
*C02F 1/44* (2006.01)

(52) U.S. Cl. ...................... 604/6.11; 210/645; 210/739; 210/741; 604/4.01; 604/5.01

(58) Field of Classification Search ................ 604/4.01, 604/5.01, 6.11; 210/645, 739, 741; 422/44
See application file for complete search history.

(56) References Cited

U.S. PATENT DOCUMENTS

| | | | |
|---|---|---|---|
| 4,469,593 A * | 9/1984 | Ishihara et al. | 210/96.2 |
| 6,061,590 A | 5/2000 | Krivitski | |
| 6,193,681 B1 * | 2/2001 | Davidner et al. | 604/6.08 |
| 6,217,539 B1 | 4/2001 | Goldau | |
| 6,387,324 B1 * | 5/2002 | Patterson et al. | 422/45 |

FOREIGN PATENT DOCUMENTS

| DE | 40 24 434 | 2/1992 |
|---|---|---|
| DE | 197 46 377 | 7/1999 |

* cited by examiner

*Primary Examiner*—Leslie R Deak
(74) *Attorney, Agent, or Firm*—Kenyon & Kenyon LLP

(57) ABSTRACT

A method for determining the hematocrit and/or blood volume during an extracorporeal blood treatment with an extracorporeal blood circuit, in which blood is taken with a blood pump via an arterial cannula and an arterial flexible-tube line and blood is fed back via a venous flexible-tube line and a venous cannula. Pressure is measured in the extracorporeal blood circuit and a change in the hematocrit is determined from a change in the pressure. The respective relationship between hematocrit HKT or blood volume RBV and pressure P in the extracorporeal circuit is stored for various cannula diameters and various blood-flow values. The respective relationship for a given cannula diameter and blood flow is selected. The hematocrit and/or blood volume is determined taking account of the selected relationship.

22 Claims, 6 Drawing Sheets

SYSTEM AND METHOD FOR DETERMINING THE HEMATOCRIT AND/OR BLOOD VOLUME

CROSS-REFERENCE TO RELATED APPLICATIONS

This application claims priority to and is a continuation of U.S. patent application Ser. No. 10/507,033, filed 7 Sep. 2004, now abandoned which is a national stage entry of PCT.EP03/00126, filed 9 Jan. 2003.

FIELD OF THE INVENTION

The invention relates to a method for determining the hematocrit and/or blood volume during an extracorporeal blood treatment with an extracorporeal blood circuit and an apparatus for extracorporeal blood treatment with an extracorporeal blood circuit and a device for determining the hematocrit and/or blood volume.

BACKGROUND

For the purpose of removing substances usually eliminated with urine and for the purpose of withdrawing fluid, various methods are currently employed for machine-aided blood cleaning or blood treatment in acute or chronic kidney failure. A method employing diffusive substance transport is typically employed in the case of hemodialysis (HD), whilst a method employing convective substance transport via a membrane takes place in the case of hemofiltration (HF). Hemodiafiltration (HDF) is a combination of these two methods.

An excessively high or rapid withdrawal of fluid during hemodialysis can give rise to a possibly rapid increase in blood volume, which often leads to an acute drop in blood pressure (hypotony) in the patient.

Hypotony represents one of the main complications in the treatment of blood. Various techniques have been proposed to deal with this problem. For instance, one technique employs blood pressure monitors which continuously monitor a change in blood pressure and regulate the ultrafiltration depending on the change in blood pressure. In another technique, blood volume monitors measure the relative blood volume during the dialysis treatment and perform a regulation of the ultrafiltration depending on the relative blood volume.

German Patent No. DE-C-197 46 377 describes a device for the measurement of blood pressure. This device is based on the detection of the propagation rate of the pulse waves being propagated via the arterial vessel system of the patient, these pulse waves being generated by the patient's heart contractions. The device permits a continuous, non-invasive measurement of blood pressure. One drawback of this device is that the pulse-wave running time is dependent on the hematocrit (HKT).

German Patent No. DE-A-40 24 434 describes a device for the regulation of ultrafiltration. With this device, the pressure in the extracorporeal circuit is measured in order to determine the relative blood volume. The measured pressure values are stored in chronological sequence and the change in the blood volume is determined from a change in the pressure value compared with the value at the start of the treatment. The venous return-flow or arterial suction-pressure sensor may be used as a pressure sensor. The reference describes that the drop in pressure on the arterial cannula is a function of the blood flow and the viscosity of the blood as well as a function both of the diameter and length of the cannula. It is also described or suggested that the relationship between the blood volume and the change in pressure is a substantially linear relationship.

One problem underlying the invention is to provide a method that permits the hematocrit and/or blood volume to be determined with a particularly high degree of accuracy, but with a relatively low technical outlay. Moreover, it is a problem of the invention to provide an apparatus for extracorporeal blood treatment with a device for determining the hematocrit and/or blood volume, which has a relatively simple construction, but a high degree of accuracy.

SUMMARY OF THE INVENTION

For reasons of safety, currently employed dialysis devices measure and monitor the arterial pressure $P_{art}(t)$ and the venous pressure $P_{ven}(t)$ in the extracorporeal blood circuit. Moreover, the rate $BPR(t)$ of the blood pump is also measured during the blood treatment, e.g., it may be employed as a control value. The present invention, according to one embodiment thereof, employs the pressure measurement that is already typically available, so that the cost of equipment is relatively low.

Generally, the monitoring of the hematocrit and blood volume through the measurement of pressure is based on the following: if a relative blood volume diminishes during a blood treatment as a result of ultrafiltration, the hematocrit in the blood necessarily increases, since the dialysis membrane is not permeable for the blood cells, namely erythrocytes (7.5 µm), leukocytes (1.5-20 µm) and thrombocyte (2.5 µm). Furthermore, the viscosity increases over-proportionately with increasing hematocrit. Since the flow resistance increases in a markedly linear manner with viscosity, each increase in the hematocrit caused by the reduction in blood volume signifies an increased load on the blood pump, which leads to the fall in the arterial pressure (negative) and the increase in the venous pressure (positive), insofar as the blood pump is operated at the same rate.

It has been determined that the relationship between blood volume or hematocrit and pressure in the extracorporeal blood circuit is dependent not merely on the blood flow, but may also be dependent on the cannula dimensions, whereby the cannula is to be regarded as the component of the extracorporeal system determining the drop in pressure. Furthermore, it has been determined that the length of the cannula does not have any significant influence on the pressure in the extracorporeal circuit, but rather that the diameter of the cannula is determinative.

According to one embodiment of the present invention, in order to improve accuracy, the respective relationship between hematocrit or blood volume and pressure is stored for different diameters of the cannula and different values of the blood flow. The respective data are thereby made readily available, even prior to the dialysis treatment. Based upon the respective diameter of the cannula and the value of the blood flow, the respective relationship between hematocrit or blood volume and pressure is then selected. The hematocrit and/or blood volume may then be determined taking account of the selected relationship. The data can for example be stored in the form of groups of curves, which can be described in particular by discrete measurement values.

Thus, an increased accuracy may result because in addition to the blood flow during the treatment, the cannula used is also considered.

In connection with hematocrit and blood volume, both absolute values as well as relative values are referred to here, which indicate a relative change in the blood volume in respect of a predetermined initial value, for example the start of the blood treatment.

An evaluation of the clinical data has demonstrated unexpectedly that in practice the arterial pressure, which is measured in the arterial blood line upstream of the blood pump, correlates with the relative blood volume much better than the venous pressure in the venous blood line. It has been ascertained that this may result from the venous pressure being very much more susceptible to interference than the arterial pressure. In the case of dialysis machines which make use of balancing chambers, the venous pressure sensor detects pressure fluctuations which are caused not only by the ultrafiltration, but also by switching balancing chambers. The air volume, or more precisely the level in the venous drip chamber, also has a strong influence on the characteristic of the venous pressure signal. In contrast, the arterial pressure is free from such pressure fluctuations. While the arterial pressure signal is influenced by the blood pumping rate, this may be an unequivocal source of interference whose influence on the arterial pressure can be compensated for.

It has been determined that the cannula diameter can be determined unequivocally by evaluating the pressure changes in the extracorporeal blood circuit. In order to determine the cannula diameter, the change in pressure resulting from a change in the blood flow is determined and the cannula diameter is determined from the change in pressure. For this purpose, the pressures are preferably measured at at least two different values of the blood flow in each case, and the difference between the pressures is calculated. In order to determine the cannula diameter, the difference in the pressures is compared with predetermined stored value ranges representative of the individual cannula diameters. The individual value ranges can be assigned unequivocally to the different cannula diameters. The relationship between cannula diameter and value range can in principle be verified again by several measurements.

Furthermore, it has been determined that the relationship between hematocrit or blood volume and pressure for different diameters of the cannula and different values of the blood flow can be determined with a sufficient degree of accuracy by a non-linear function, for example a second-order polynomial. Since the blood flow correlates with the rate of the blood pump, the pumping rate, which is preset by the control of the blood treatment device, is preferably used to determine the blood flow.

When the hematocrit is determined, the blood volume can be calculated. The blood volume is calculated at a specified time in the blood treatment from the product of the hematocrit at a preceding time and the blood volume at a preceding time divided by the hematocrit at the specified time.

The device for determining the hematocrit and/or blood volume of the apparatus for extracorporeal blood treatment, according to one embodiment of the present invention, has a memory and evaluation unit, in which the respective relationships between hematocrit and blood volume for the different cannula diameters and blood flows are stored. Such a memory and evaluation unit can be part of a computer control, which may already be present in a currently employed blood treatment apparatus. The measurement of the pressure preferably takes place with a pressure sensor which may also already be present.

The determination of the cannula diameter on the basis of a pressure measurement is of particular significance. This knowledge of the influence of the cannula can be used in an advantageous way, e.g., with a method for blood pressure measurement described in German Patent No. DE-C-197 46 377. The influence of the blood density on the pulse-wave running time is compensated for or corrected so that the blood pressure measurement takes place with a high degree of accuracy.

BRIEF DESCRIPTION OF THE DRAWINGS

One example embodiment of an extracorporeal blood treatment apparatus with a device for determining the hematocrit and/or blood volume as well as an example of embodiment of the method according to the invention are explained below in greater detail with the aid of the figures.

The figures show the following.

DETAILED DESCRIPTION

Figure 1:
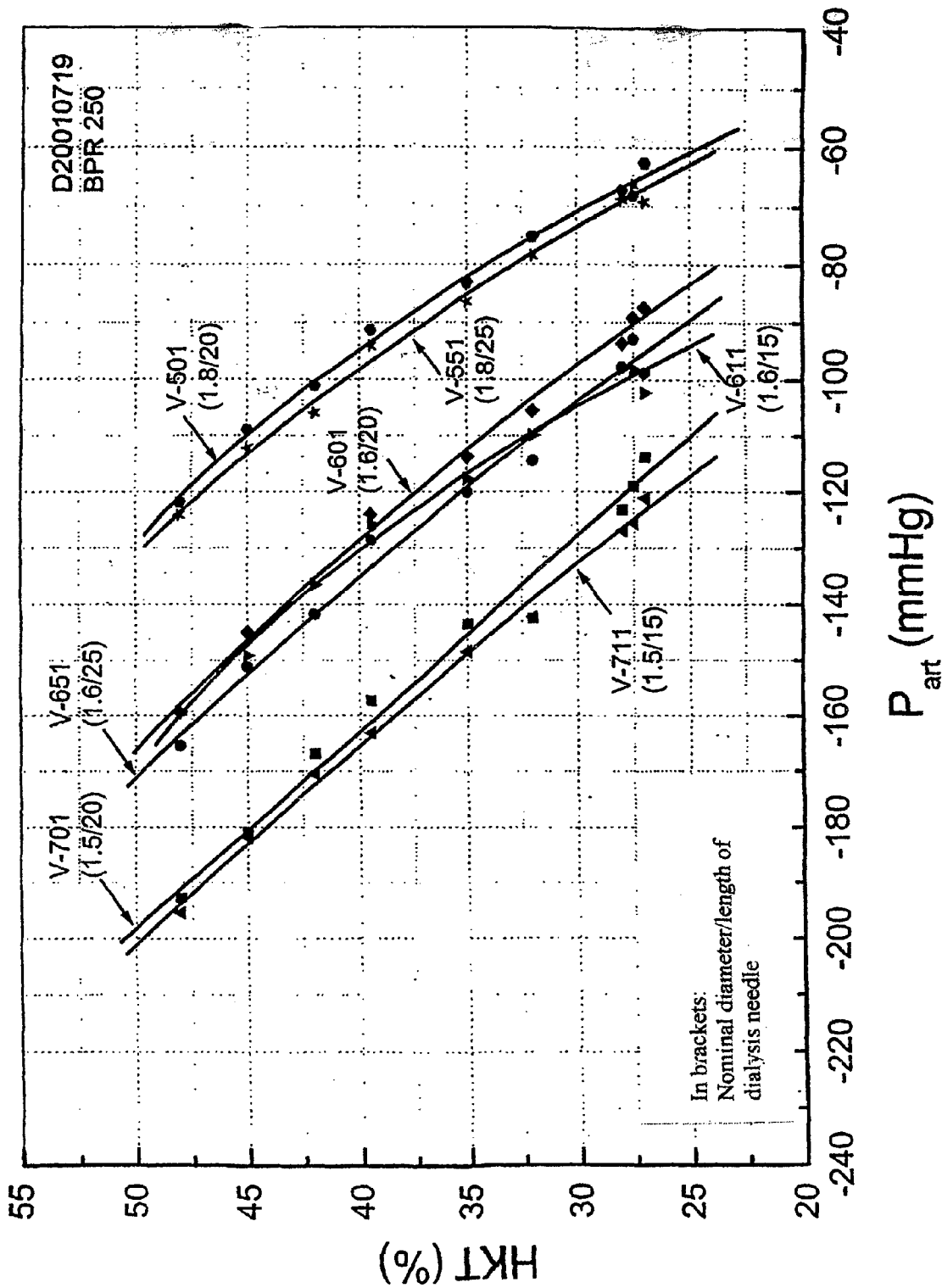
FIG. 1 is a graph that illustrates the hematocrit (HKT (%)) as a function of the arterial pressure ($P_{art}$(mmHg)) for various cannulas of differing diameter and differing length, according to one embodiment of the present invention.

FIG. 1 is a graph that illustrates the relationship between the hematocrit (HKT (%)) of the blood and the pressure in the arterial blood line of the extracorporeal circuit with a constant blood pumping rate BPR of 250 ml/min. for seven different dialysis cannulas, which differ from one another in diameter and length. For example, the cannula with the designation V-711 has a diameter of 1.5 mm and a length of 15 mm. The other cannulas are correspondingly designated in FIG. 1. It can be seen in FIG. 1 that the relationship between hematocrit and arterial pressure is not linear. It can, however, be described to a good approximation by a second-order polynomial. Furthermore, it can be seen that the relationship between hematocrit and pressure depends markedly on the diameter of the cannulas. The influence of the length of the cannulas, on the other hand, is relatively small. The influence of the length of the cannulas can therefore be neglected without significantly effecting accuracy. For this reason, the relationship is grouped markedly according to the diameter of the cannulas, e.g., 1.5, 1.6 and 1.8 mm, respectively. Due to the marked dependence of the relationship on the diameter of cannulas, the measurement of the pressure for the determination of the hematocrit or blood volume without a knowledge of the cannula diameter may lead to inaccurate results.

Figure 2:
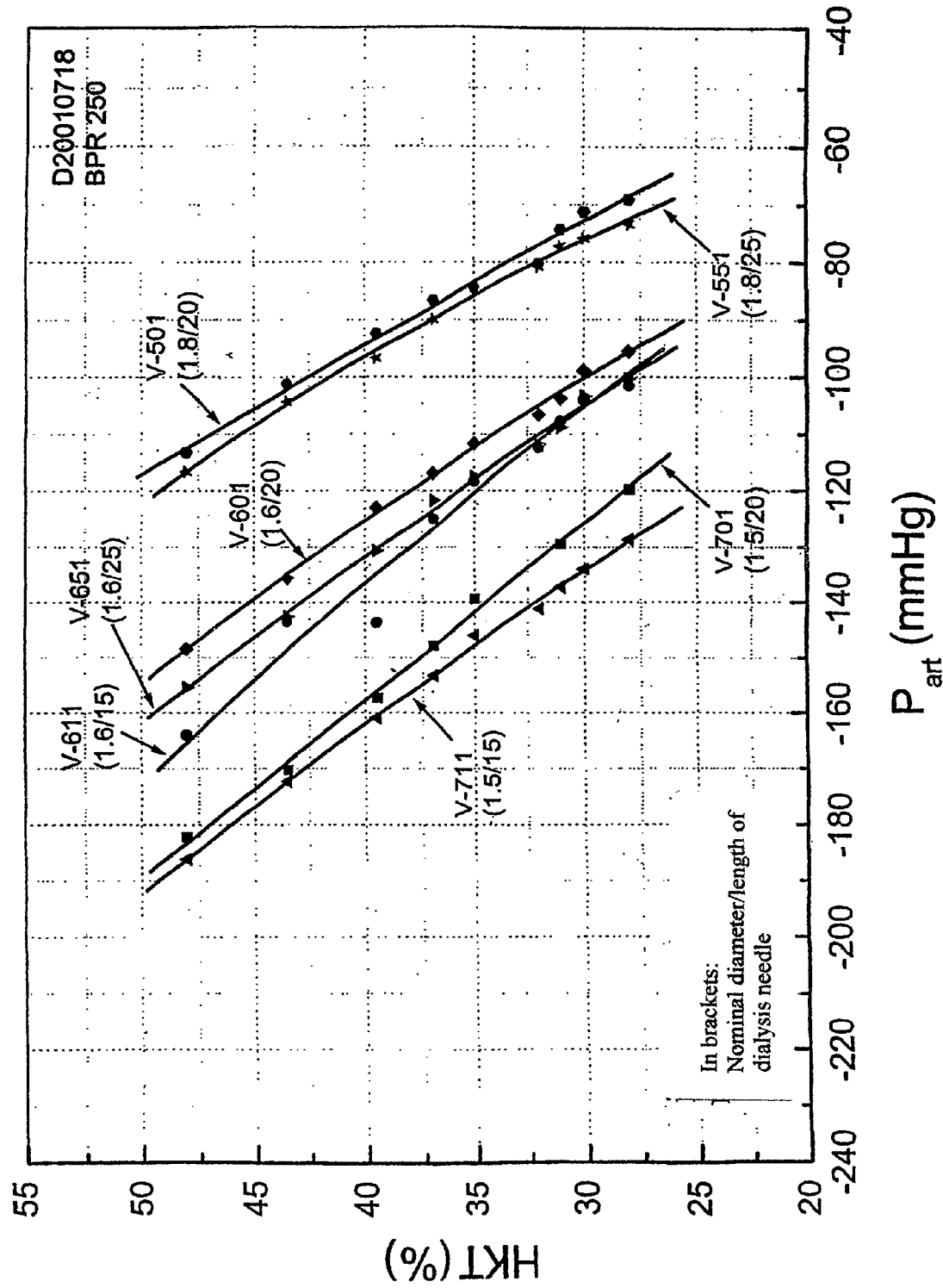
FIG. 2 is a graph that illustrates the hematocrit (HKT (%)) as a function of the arterial pressure ($P_{art}$(mmHg)) for various cannulas, according to one embodiment of the present invention.

FIG. 2 shows the relationship of hematocrit and arterial pressure of a second measurement series with a blood flow rate BPR of 250 ml/min. Here too, the grouping according to the cannula diameters is distinctly marked.

Figure 3:
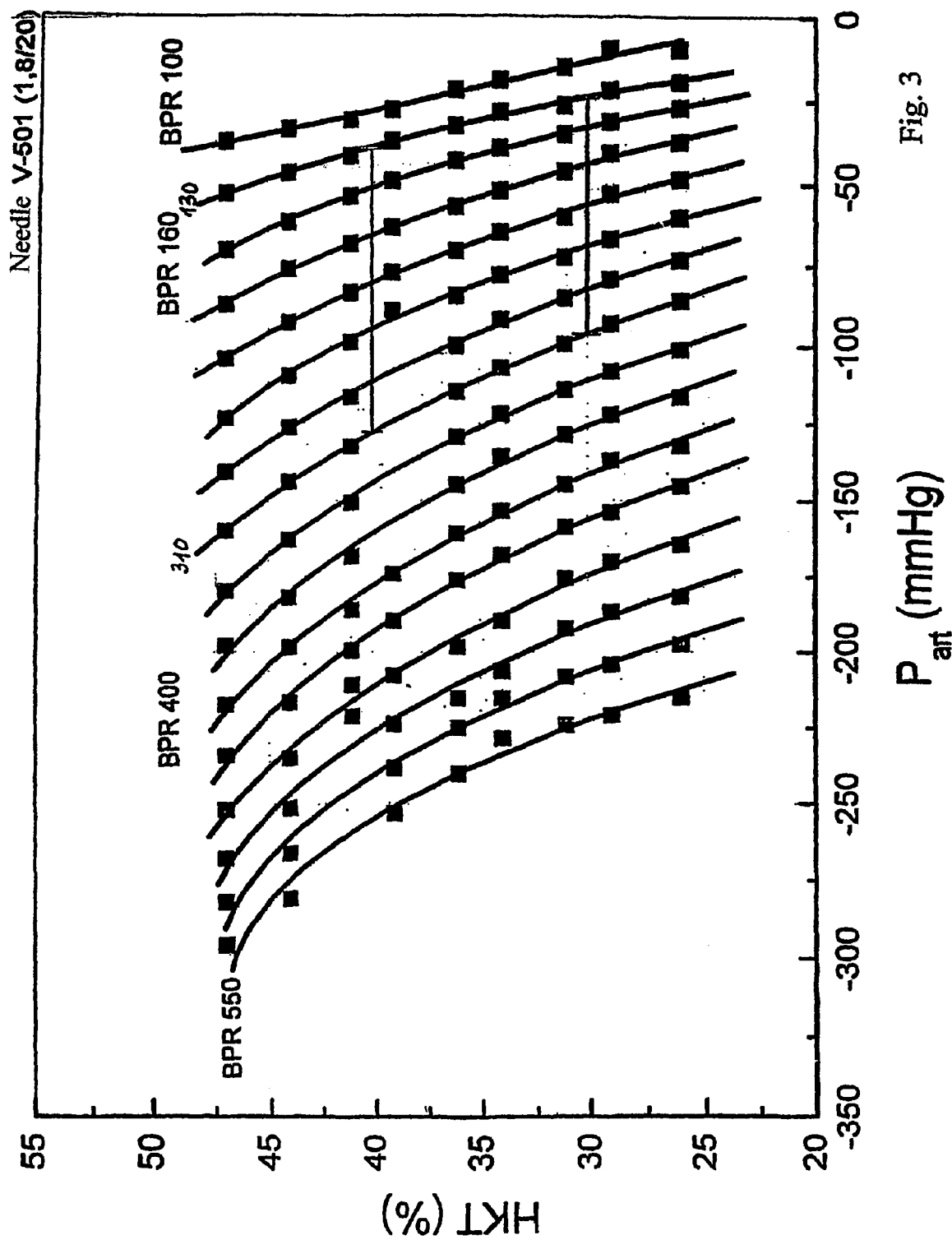
FIG. 3 is a graph that illustrates the hematocrit (HKT (%)) as a function of the arterial pressure ($P_{art}$(mmHg)) for various values of the blood flow with a first cannula, according to one embodiment of the present invention.

FIG. 3 shows the relationship between hematocrit (HKT (%)) and arterial pressure ($P_{art}$(mmHg)) in the case of a needle with a diameter of 1.8 mm and a length of 20 mm for a large number of blood flows BPR between 100 ml/min. and 550 ml/min. Here too, the relationship is not linear. It can however again be described to a good approximation by a second-order polynomial. In a range of blood flow from 160 to 400 ml/min., the curves for different blood flows exhibit a similar gradient. Since the dependence of the blood flow, e.g., the blood pumping rate, is essentially expressed by the fact that the curves are displaced parallel to the x-axis and that the displacement is dependent on the diameter of the needle, the needle diameter can be determined unequivocally. On the assumption that the hematocrit of a dialysis patient lies in the range from 30% to 40%, the diameter of the cannula can be detected without knowledge of the hematocrit. The detection takes place via measurement of the pressure difference with two different blood flows, i.e. blood pumping rates, whereby typical values lie between 130 ml/min. and 310 ml/min.

Figure 4:
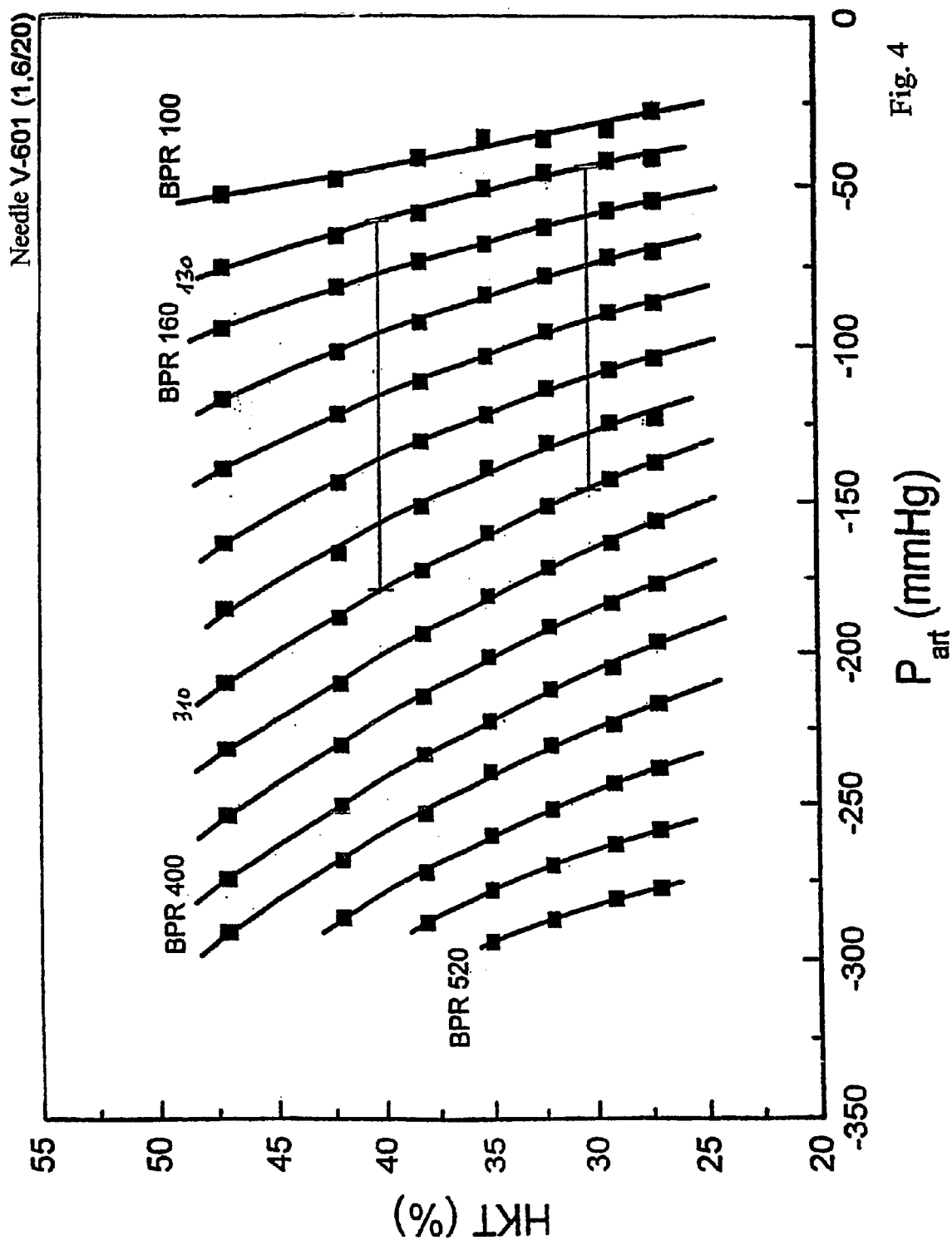
FIG. 4 is a graph that illustrates the hematocrit (HKT (%)) as a function of the arterial pressure ($P_{art}$(mmHg)) for various values of the blood flow with a second cannula, according to one embodiment of the present invention.
Figure 5:
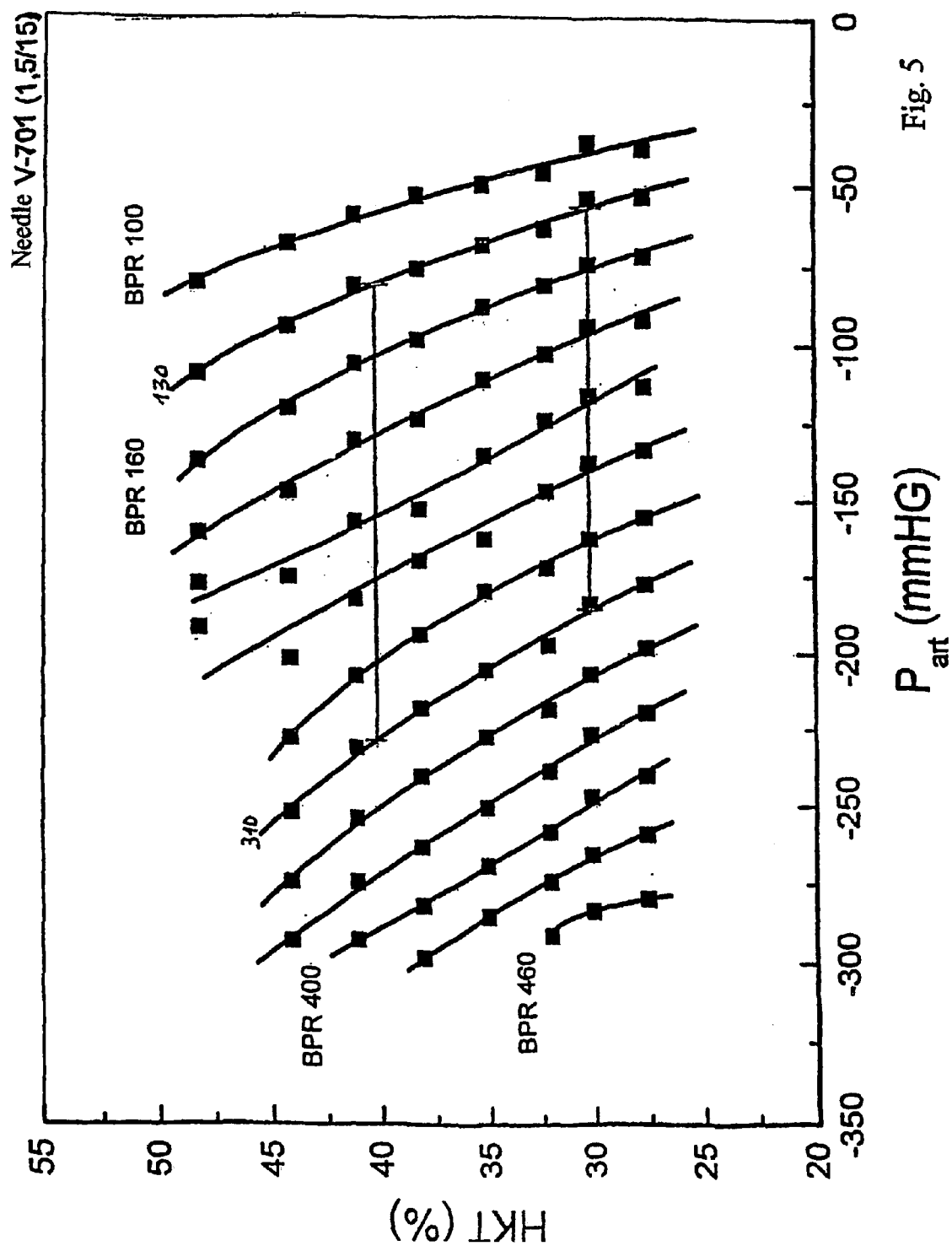
FIG. 5 is a graph that illustrates the hematocrit (HKT (%)) as a function of the arterial pressure ($P_{art}$(mmHg)) for various values of the blood flow with a third cannula, according to one embodiment of the present invention.

FIGS. 4 and 5 show the groups of curves of a needle with a diameter of 1.6 mm and a length of 20 mm and a needle with a diameter of 1.5 mm and length of 15 mm, respectively.

The determination of the cannula diameter with the aid of the groups of curves in FIGS. 3 to 5 is explained in greater detail below. Arterial pressures $P_{art1}$ and $P_{art2}$ are measured for this purpose at at least two predetermined blood pumping rates BPR1 and BPR2. The difference $\Delta P_{art} = \Delta P_{art1} - P_{art2}$ is then calculated, which is represented in FIGS. 3 to 5 as a horizontal bar. Values for $\Delta P_{art}$ that can be assigned with substantial certainty to the individual cannula diameters arise for an HKT range of approximately 30 to 40%. These value ranges are previously determined and stored, whereby an appropriate assignment is carried out after measurement of the change in pressure.

The following table shows the pressure difference $\Delta P_{art}$ (mmHg) for the three cannulas of differing diameter (1.8, 1.6 and 1.5 mm) with a hematocrit HKT of 30 and 40%. The measurement magnitudes can be grouped into the value ranges 70 to 90 mmHg for a cannula diameter of 1.8 mm, 100 to 120 mmHg for a cannula diameter of 1.6 mm and 130 to 150 mmHg for a cannula diameter of 1.5 mm. After measurement of pressure difference $\Delta P_{art}$, it can thus be determined with substantial certainty the diameter of the cannula. It emerges that the hematocrit does not have any influence on the unambiguousness of the detection of the needle diameter when it lies in the physiological range between 30 and 40%.

| | $\Delta P_{art}$(mmHg) | | |
|---|---|---|---|
| HKT (%) | V-501 (Ø 1.8 mm) | V-601 (Ø 1.6 mm) | V-701 (Ø 1.5 mm) |
| 30 | 72 | 102 | 130 |
| 40 | 89 | 118 | 148 |

Figure 6:
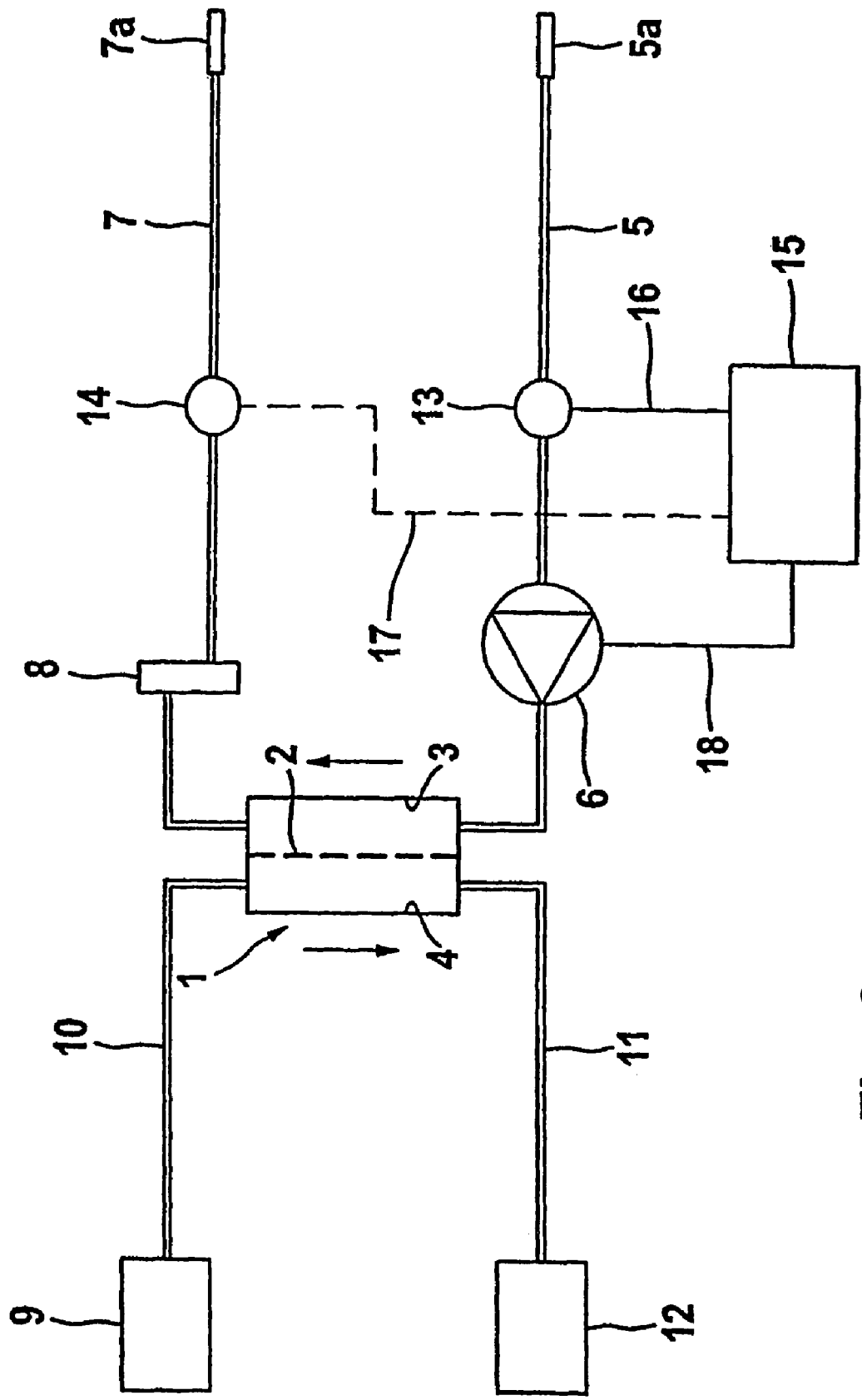
FIG. 6 is a diagram that illustrates generally the salient features of an extracorporeal blood treatment apparatus with a device for determining the hematocrit and/or blood volume, according to one embodiment of the present invention.

FIG. 6 is a diagram that illustrates, according to one embodiment of the present invention, some of the components of an extracorporeal blood treatment apparatus together with a device for determining the hematocrit and/or blood volume.

As a blood treatment device, the dialysis apparatus has a dialyser 1, which is divided by a semipermeable membrane 2 into a blood chamber 3 and a dialysis-fluid chamber 4. An arterial blood line 5 leads to the inlet of blood chamber 3. A peristaltic blood pump 6 is connected into the arterial blood line. A venous blood line 7 leads off from blood chamber 3. A drip chamber 8 is connected into the venous blood line 7. To the ends of the arterial and venous blood line 5, 7, there are connected cannulas 5a, 7a, which are inserted into the patient. The arterial and venous blood line may be a component of a flexible-tube line system designed to be disposable.

Fresh dialysis fluid is prepared in a dialysis-fluid source 9. A dialysis-fluid supply line 10 leads from dialysis-fluid source 9 to an inlet of dialysis-fluid chamber 4 of the dialyser, whilst a dialysis-fluid discharge line 11 leads from the outlet of the dialysis-fluid chamber to a drain 12. The dialysis apparatus also has further components, e.g. a balancing device and an ultrafiltration device etc., which however are not represented for the sake of better clarity. Moreover, the central control unit, which is a component of the dialysis apparatus, is not represented.

For safety reasons, the arterial pressure in arterial blood line 5 is monitored upstream of blood pump 6 and the venous pressure in the venous blood line is monitored downstream of drip chamber 8 in the dialysis apparatus. For this purpose, an arterial pressure sensor 13 is provided in arterial blood line 5 and a venous pressure sensor 14 is provided in venous blood line 7. The device for determining the hematocrit and/or blood volume includes arterial pressure sensor 13, which may already be available, e.g., in the dialysis apparatus and/or the memory and evaluation unit 15. The memory and evaluation unit 15 receives the pressure signal of arterial pressure sensor 13 via a data line 16. Alternatively, the memory and evaluation unit can receive the pressure signal of a venous pressure sensor 14 via a data line 17. Data line 17 is shown by a dashed line in FIG. 6. Furthermore, memory and evaluation unit 15 is connected to blood pump 6 via a data line 18. A blood pump signal proportional to the blood pumping rate is transmitted via data line 18. The curve groups represented in FIGS. 3 to 5, which describe the relationship between hematocrit and arterial pressure, are stored in the memory and evaluation unit 15.

According to one embodiment of the present invention, the memory and evaluation unit 15 operates in the following manner.

The cannula diameter, in which the blood pumping rate is varied, is first determined in an initial measurement during the dialysis treatment, whereby the arterial pressures $P_{art1}$ and $P_{art2}$ are measured at two predetermined blood pumping rates BPR of, for example, 310 and 130 ml/min. (FIG. 3). The memory and evaluation unit calculates from the measured values the amount of the pressure difference $\Delta P_{art} = P_{art1} - P_{art2}$, which in the present example amounts to 89 mmHg with a hematocrit of 40%. In principle, however, measurements can also be carried out for other hematocrit values, insofar as the hematocrit lies in the physiological range of the patient and thus between 30 and 40%.

In addition to the groups of curves, there may also be stored in the memory and evaluation unit 15 the value ranges from 70 to 90, 100 to 120 and 130 to 150 mmHg characteristic of the cannula diameter, which are described above. The memory and evaluation unit performs an assignment between the measured pressure difference $\Delta P_{art}$ and the stored value ranges. Since the measured pressure difference $\Delta P_{art}$ lies here in the value range between 70-90 mmHg, the memory and evaluation unit assumes that the cannula has a diameter of 1.8 mm (FIG. 3).

After the cannula diameter has been ascertained in the initial measurement, the memory and evaluation unit 15 may carry out a selection between the different curve groups (FIGS. 3 to 5), which respectively describe the relationship of hematocrit and arterial pressure for the respective needle diameter. The memory and evaluation unit 15 selects here the group of curves according to FIG. 3, which are representative of the present needle diameter of 1.8 m After the selection of the appropriate curve group, the memory and evaluation unit 15 determines from the appropriate curve group, with a high degree of accuracy, the appropriate hematocrit in dependence on the blood pumping rate BPR(t) taking account of the diameter of the employed cannula, without the diameter of the used cannula needing to be inputted manually. If, for example, an arterial pressure of 100 mmHg is measured with the arterial pressure sensor, a hematocrit of approx. 33% results with a blood pumping rate of 310 ml/min. (FIG. 3). With decreasing blood pumping rate, the hematocrit increases according to the curve group.

The determination of the blood volume takes place after the hematocrit has been ascertained. The blood volume at a specified time in the blood treatment RBV(t) is calculated from the hematocrit HKT according to the following equation:

$$RBV(t) = \frac{HKT(t_o)RBV(t_0)}{HKT(t)}$$

whereby RBV(t) is the blood volume at time t, HKT(t) is the hematocrit at time t, and RBV($t_o$) and HKT($t_o$) are respectively the blood volume and the hematocrit at an arbitrary time $t_o$, which lies before time t. Since RBV ($t_o$)=1 at the start of the dialysis treatment, the memory and evaluation unit 15 can determine RBV(t) relative to this time. On the other hand, the above equation can also be used for two arbitrary times $t_o$ and t if $t_o$ does not coincide with the start of the treatment and RBV($t_o$) is thus not necessarily 1. If RBV ($t_o$) is not known, the memory and evaluation unit 15 can however determine relative changes in RBV according to the above equation compared with a value of RBV($t_o$) of 1.

The invention claimed is:

1. A method for determining at least one of hematocrit and blood volume during an extracorporeal blood treatment with an extracorporeal blood circuit, comprising the steps of:
    taking blood from a patient with a blood pump via an arterial cannula and an arterial line;
    providing the blood back to the patient via a venous line and a venous cannula;
    measuring an arterial pressure; and
    determining a hematocrit value and/or blood volume value from the arterial pressure by:
    selecting a relationship for a given cannula diameter and a given blood flow from a plurality of relationships between hematocrit HKT or blood volume RBV and pressure P in the extracorporeal circuit that are stored for various cannula diameters and various blood-flow values; and
    determining the hematocrit and/or blood volume at the arterial pressure in accordance with the selected relationship.

2. The method according to claim 1, wherein the step of measuring the arterial pressure $P_{art}$ is done in the arterial flexible-tube line upstream of the blood pump.

3. The method according to claim 1, wherein the plurality of relationships between hematocrit HKT or blood volume RBV and pressure P in the extracorporeal circuit are determined by performing the following steps for a plurality of cannula diameters:
    setting a first blood flow rate in the extracorporeal blood circuit;
    measuring a first pressure in the extracorporeal blood circuit when the blood is provided at the first blood flow rate and at a first predetermined hematocrit value;
    changing the blood flow rate to a second blood flow rate in the extracorporeal circuit; and
    measuring a second pressure in the extracorporeal blood circuit when the blood is provided at the second blood flow rate and at the first predetermined hematocrit value.

4. The method according to claim 3, further comprising: calculating the pressure difference between the first arterial pressure and the second arterial pressure.

5. The method according to claim 4, further comprising: comparing the pressure difference at the first hematocrit value to a pre-calculated table, said pre-calculated table showing the relationship between the pressure difference and the hematocrit value for a plurality of cannula diameters, in order to determine the cannula diameter.

6. The method according to claim 3, wherein the first hematocrit value is between 30% and 40%.

7. The method according to claim 3, further comprising:
    changing the blood flow rate to a third blood flow rate in the extracorporeal circuit; and
    measuring a third arterial pressure in the extracorporeal blood circuit when the blood is provided at the third blood flow rate and at the first hematocrit value.

8. The method according to claim 7, further comprising: calculating the pressure difference between the second arterial pressure and the third arterial pressure.

9. The method according to claim 8, further comprising: determining the cannula diameter by comparing the pressure difference at the first hematocrit value to a pre-calculated table, said pre-calculated table showing the relationship between the pressure difference and the hematocrit value for a plurality of cannula diameters.

10. The method according to claim 1, wherein the relationship between hematocrit or blood volume and pressure for various diameters of the cannula and various values of the blood flow is described by a non-linear function.

11. The method according to claim 1, further comprising: determining a pumping rate BPR of the blood pump in order to determine a blood flow.

12. The method according to claim 1, wherein the blood volume RBV is determined from the hematocrit HKT.

13. The method according to claim 12, further comprising: calculating the blood volume RBV at a specified time t of the blood treatment from the product of HKT($t_o$) and RBV($t_o$), divided by the hematocrit HKT(t), wherein HKT($t_o$) is the hematocrit value at a first time $t_o$ and RBV($t_o$) is the blood volume at the first time $t_o$, and HKT(t) is the hematocrit value at the specified time t.

14. An apparatus for extracorporeal blood treatment with an extracorporeal blood circuit, comprising:
    a blood pump;
    an arterial cannula and an arterial line for taking blood from a patient;
    a venous cannula and venous line for providing back blood to the patient;
    a device for determining the hematocrit and/or blood volume, the device having:
    a pressure sensor for measuring the arterial pressure in the extracorporeal circuit; and
    a memory and evaluation unit configured such that a change in the hematocrit or blood volume is deduced from a change in the pressure, wherein the respective relationship between hematocrit HKT or blood volume RBV and pressure P in the extracorporeal circuit is stored for various cannula diameters and various blood-flow values in the memory and evaluation unit, and wherein the memory and evaluation unit is configured such that the appropriate relationship is selected for the respective cannula diameter and blood flow and hematocrit and/or blood volume is determined in accordance with the selected relationship.

15. The apparatus according to claim 14, wherein the pressure sensor is arranged in the arterial blood line upstream of the blood pump.

16. The apparatus according to claim 14, wherein the memory and evaluation unit has stored thereon a pre-calculated table showing the relationship between the pressure difference and the hematocrit value for a plurality of cannula diameters.

17. The apparatus according to claim 16 , wherein the memory and evaluation unit is configured such that, in order to determine the cannula diameter, a first pressure is measured at a first hematocrit value and a first blood flow rate, and a second pressure is measured at the first hematocrit value and a second blood flow rate, and a change in the arterial pressure resulting from a change in the blood flow is determined.

18. The apparatus according to claim 17, wherein the memory and evaluation unit is configured such that pressures $P_{art1}$ and $P_{art2}$ are measured at at least two different values of blood flow and the difference $\Delta P_{art} = P_{art1} - P_{art2}$ is calculated from the pressures $P_{art1}$ and $P_{art2}$, whereby the difference $\Delta P_{art}$ is compared with the predetermined table in order to determine the cannula diameter.

19. The apparatus according to claim 14, wherein the memory and evaluation unit is configured such that the relationship between hematocrit HKT or blood volume RBV and pressure for various cannula diameters and various blood-flow values is described by a non-linear function.

20. The apparatus according to claim 14, wherein the memory and evaluation unit is configured such that a pumping rate BPR of the blood pump is determined in order to determine a blood flow.

21. The apparatus according to claim 14, wherein the memory and evaluation unit is configured such that the blood volume RBV is determined from the hematocrit HKT.

22. The apparatus according to claim 21, wherein the memory and evaluation unit is configured such that the blood volume RBV is calculated at a specified time t of the blood treatment from the product of $HKT(t_o)$ and $RBV(t_o)$, divided by the hematocrit $HKT(t)$ at the specified time t, wherein $HKT(t_o)$ is the hematocrit value at a first time $t_o$ and $RBV(t_o)$ is the blood volume at the first time $t_o$, and $HKT(t)$ is the hematocrit value at the specified time t.

* * * * *